United States Patent [19]

Kallok et al.

[11] Patent Number: 5,146,918
[45] Date of Patent: Sep. 15, 1992

[54] DEMAND APNEA CONTROL OF CENTRAL AND OBSTRUCTIVE SLEEP APNEA

[75] Inventors: Michael J. Kallok, New Brighton; H. Toby Markowitz, Roseville, both of Minn.

[73] Assignee: Medtronic, Inc., Minneapolis, Minn.

[21] Appl. No.: 671,513

[22] Filed: Mar. 19, 1991

[51] Int. Cl.$^5$ ............................................. A61N 1/00
[52] U.S. Cl. ................................... 128/419 G; 128/421
[58] Field of Search ........... 128/419 G, 421, 720–721, 128/716, 204.23

[56] References Cited

U.S. PATENT DOCUMENTS

| | | | |
|---|---|---|---|
| 1,410,761 | 10/1922 | Prud'Homme | 128/419 G |
| 2,711,729 | 6/1955 | Hofmann | 128/419 G |
| 4,506,666 | 3/1985 | Durkan . | |
| 4,570,631 | 2/1986 | Durkan . | |
| 4,765,340 | 8/1988 | Sakai et al. | 128/716 |
| 4,830,008 | 5/1989 | Meer . | |

FOREIGN PATENT DOCUMENTS 8600234  1/1986  France .............................. 128/419 G

OTHER PUBLICATIONS

"Addition to an RF-coupled phrenic nerve stimulator implant to provide outward transmission of body temperature." Medical & Biological Engineering; Nov. 1986; 24, 659–661.

Glenn, William W. L., Diaphragm Pacing: Present Status, 1977.

Cook, William R., & Osquthorpe, J. David, Obstructive Sleep Apnea: Diagnosis and Treatment, Dec. 1985.

*Primary Examiner*—William E. Kamm
*Assistant Examiner*—J. R. Jastrzab
*Attorney, Agent, or Firm*—Harold R. Patton; Daniel W. Latham; John L. Rooney

[57] ABSTRACT

An apparatus and method for the control of both central and obstructive sleep apnea using electrical stimulation on a demand basis. Implantable sensors monitor the respiration cycle and determine the occurrence of apnea events. Central apnea is sensed by the passage of an escape interval of time without the sensing of an inspiratory event and a concurrent decrease in blood oxygen saturation. Obstructive sleep apnea is sensed as an abnormal pressure differential across the airway. The diaphragm is electrically stimulated upon sensing of central apnea. The musculature of the upper airway is electrically stimulated upon sensing of an occurrence of obstructive sleep apnea. Stimulation of the upper airway is provided whenever central apnea is sensed.

12 Claims, 12 Drawing Sheets

# DEMAND APNEA CONTROL OF CENTRAL AND OBSTRUCTIVE SLEEP APNEA

CROSS REFERENCE TO CO-PENDING APPLICATIONS

U.S. patent application Ser. No. 07/610,854, filed Nov. 8, 1990, entitled "Muscle Tone"; U.S. patent application Ser. No. 07/610,851, filed Nov. 8, 1990, entitled "Servo Muscle Control"; and U.S. patent application Ser. No. 07/617,158, filed Nov. 23, 1990, entitled "Multiple Stimulation Electrodes", are all assigned to the assignee of the present invention and incorporated herein by reference.

BACKGROUND OF THE INVENTION

1. Field of the Invention

The present invention relates generally to implantable medical devices, and more particularly, relates to implantable medical devices for the treatment of apnea.

2. Description of the Prior Art

The medical characteristics of sleep apnea have been known for some time. There are two generally recognized forms of the disease. The first is central sleep apnea, which is associated with the failure of the body to automatically generate the neuro-muscular stimulation necessary to initiate and control a respiratory cycle at the proper time. Work associated with employing electrical stimulation to treat this condition is discussed in "Diaphragm Pacing: Present Status", by William W. L. Glenn, in Pace, Volume I, at pages 357-370 (July-September 1978).

The second condition is known as obstructive sleep apnea. It is discussed at some length in "Obstructive Sleep Apnea: Diagnosis and Treatment", by Drs. Cook and Osguthorpe in *Journal of South Carolina Medical Association*, 81 (12): 647-651 (December 1985).

At present, a tracheostomy may be the treatment of choice for a number of patients when obstructive sleep apnea is severe. A less traumatic recent approach is continuous positive airway pressure (CPAP). This technique seeks to maintain upper airway patency with compressed air. More recently, some interest has been displayed in electrical stimulation of the muscle tissue along the upper airway during respiration. U.S. Pat. No. 4,830,008 issued to Meer discusses a technique for electrical stimulation of the muscles of the upper airway in synchrony with the respiratory cycle. U.S. Pat. No. 4,506,666 issued to Durkan discusses such stimulation in conjunction with pressurized airflow supplied by a respirator.

The electrical stimulation of the prior art techniques, however, are primarily concerned with causing contractile motion of the stimulated muscle. This means that the stimulation energy must necessarily be relatively large, and the effects of the stimulation are directly cognizable by the patient.

More significant is that prior art systems tend to be directed toward treatment of either central or obstructive sleep apnea. There exists no effective means for treating both conditions which are found together in a sizable number of patients.

SUMMARY OF THE INVENTION

The present invention overcomes the disadvantages of the prior art systems by providing an apparatus and method for treating both central sleep apnea and obstructive sleep apnea in a coordinated fashion using a single hardware system. The treatment involves monitoring the respiratory activity of the patient and supplying appropriate stimulation as required.

To monitor events of central sleep apnea, sensors are employed to detect indices of reduced or absent respiratory drive. For example, a pressure sensor implanted in the thorax can be used to detect respiratory effort. An oxygen sensor implanted in the circulatory system can be used to detect arterial oxygen saturation or mixed venous oxygen saturation, both measures decreasing during apnea. A sensing electrode implanted on the phrenic nerve can be used to detect central nervous system inspiratory drive to the respiratory muscles.

Information from these sensors can be evaluated in a decision algorithm to determine if central apnea is present. For example, lack of respiratory effort and/or phrenic nerve activity, and decreasing blood oxygen saturation are indicative of central apnea. Each of the sensors can be used individually as well. For example, lack of respiratory effort or phrenic nerve activity for a specified period of time since the last respiratory effort could indicate central apnea. Similarly, falling blood oxygen saturation could also indicate central apnea.

It should be noted however, that no single sensor is as reliable as a combination of sensors in detecting central apnea. The decision must be made whether to incur the added complexity and cost associated with multiple sensors to provide improved accuracy of apnea detection.

In response to a detected situation of central apnea, the implantable pulse generator provides stimulation pulses to electrically stimulate contraction of the diaphragm to artificially initiate inspiration.

An easy, but less accurate way to monitor events of central sleep apnea is to employ sensors to determine the time of occurrence of inspiratory and expiratory activity. An escape interval clock is used to measure the time between such activity. Whenever initiation of inspiratory activity is delayed beyond a predetermined time, it is assumed that a central sleep apnea event has occurred.

An obstructive sleep apnea event is identified by an abnormally high pressure differential across the upper airway during inspiration. As a result, the implantable pulse generator provides a train of stimulation pulses to the muscles of the upper airway to cause contraction of muscles which can separate (or open) the walls of the airway, and thereby remove the obstruction. Because the basic respiratory timing is interrupted during a central sleep apnea event, stimulation of the upper airway is always provided for respiratory cycles for which diaphragm pacing is employed.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED PREFERRED EMBODIMENTS

Figure 1:
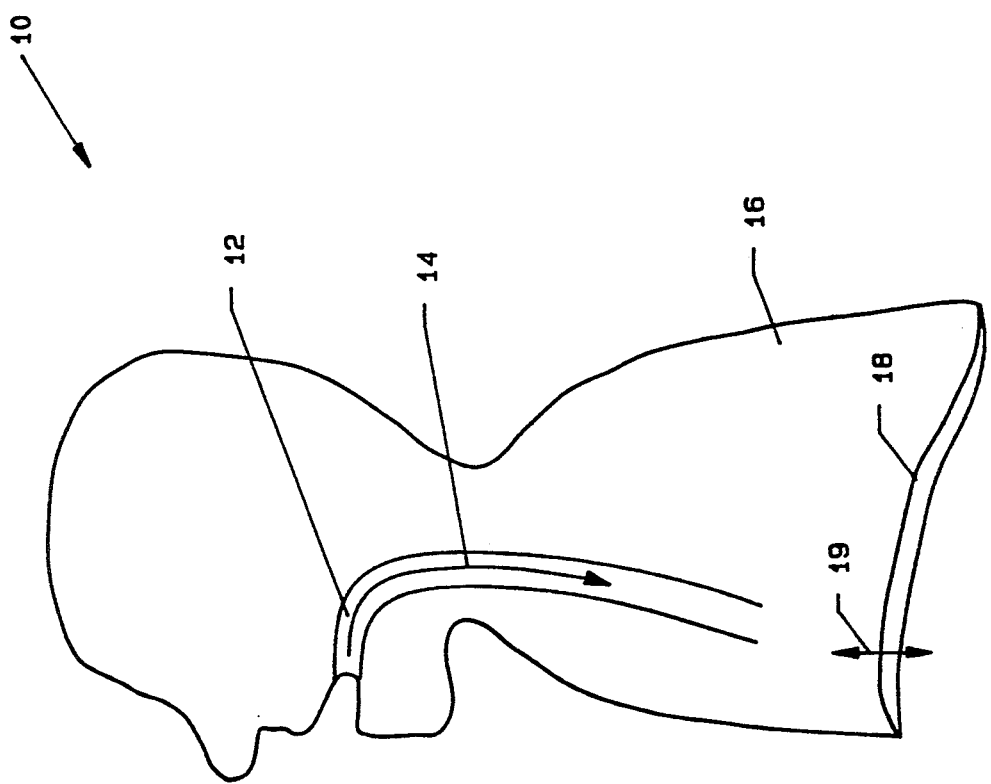
FIG. 1 is a schematic diagram of the respiratory system of a patient.

FIG. 1 is a schematic diagram of the respiratory system of patient 10 during inspiration. As a result of contraction of diaphragm 18, which increases the volume of thorax 16, a partial vacuum is created causing air to enter upper airway 12 and proceed in the direction of arrow 14. During an event of central sleep apnea, the neurological system of patient 10 fails to automatically stimulate contraction of diaphragm 18 at the appropriate time for inspiration. This condition may be sensed by monitoring the EMG of diaphragm 18, pressure difference between the thorax 16 and the ambient, airflow within upper airway 12, or other indication of inspiration at a time appropriate for inspiration.

Figure 2:
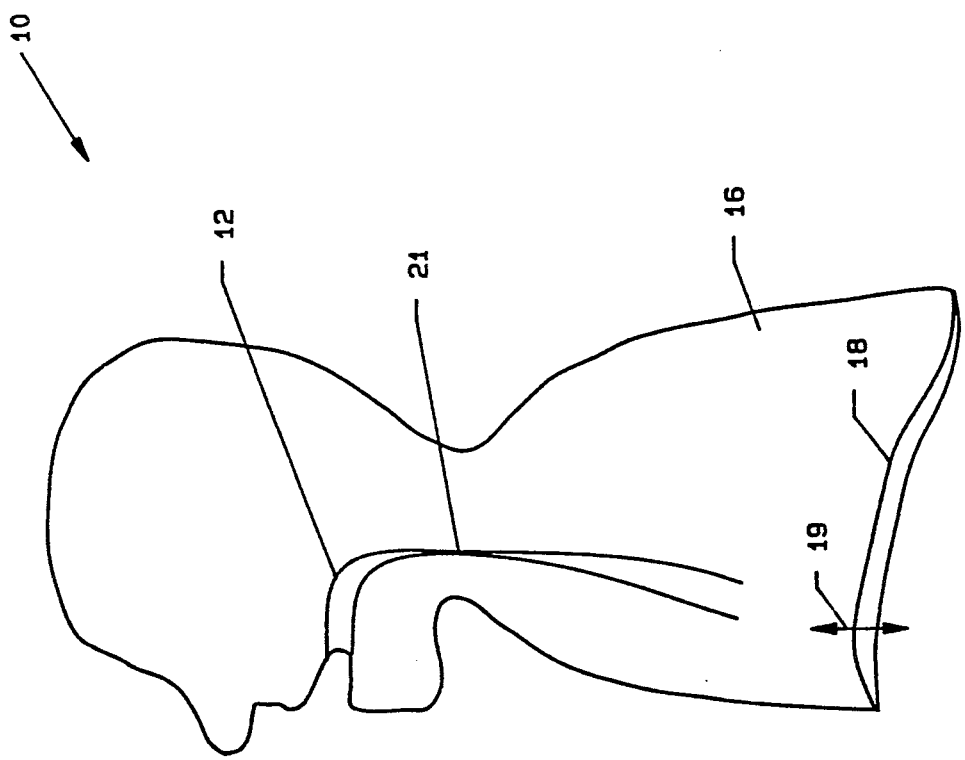
FIG. 2 is a schematic diagram of the respiratory system of a patient during an obstructive sleep apnea event.

FIG. 2 is a schematic diagram of the respiratory system of patient 10 during an obstructive apnea event. During inspiration, upper airway 12 tends to collapse producing the obstruction to air flow at point 21. The above referenced literature describes in detail the physiological processes associated with the collapse of upper airway 12.

Figure 3:
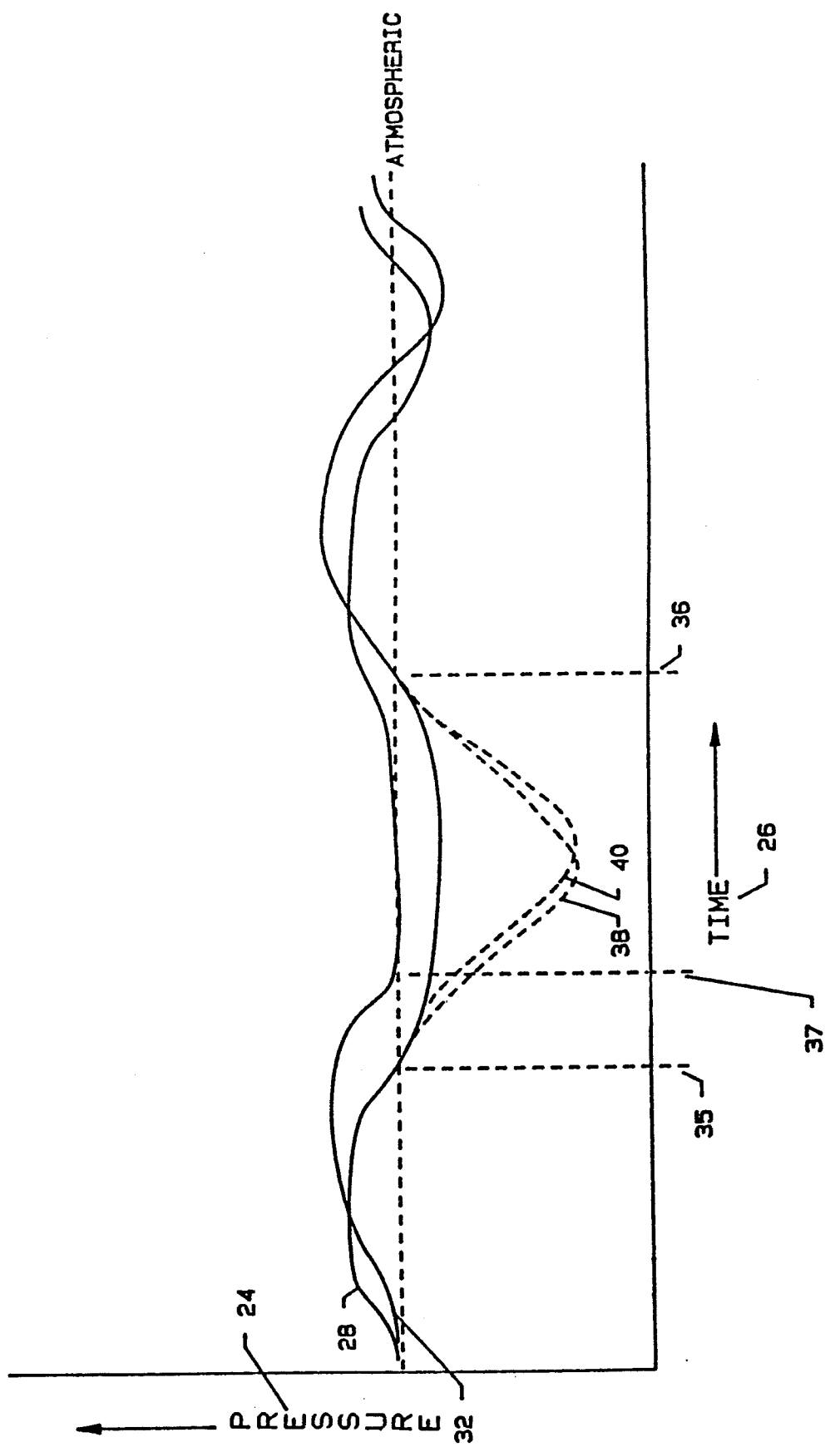
FIG. 3 is a graphical representation of pressure measurements within the upper airway.

FIG. 3 is a graphical representation for pressure 24 measured within upper airway 12 during respiration as a function of time 26. Curve 28 shows the pressure for normal functioning of the respiratory system. Time 35 represents the end of the expiration portion of the cycle. Inspiration occurs from time 35 through time 36. Curve 32 shows the pressure measurements for the patient during central sleep apnea. The delay from time 37 to time 36 may be sufficient to detect central sleep apnea. Note that because respiration is a partially voluntary function, the rate may vary substantially providing a low confidence in detection solely by this means. Because curve 32 is produced by artificial stimulation of diaphragm 18 at point 36, it results in a somewhat larger amplitude without the flat plateau at the desired pressure. This is caused by the less even contraction of diaphragm 18.

Curves 38 and 40 represent the monitored pressure during inspiration with and without central sleep apnea, respectively. Detection of obstructive sleep apnea along curve 38 can occur as soon as time 37.

Figure 4:
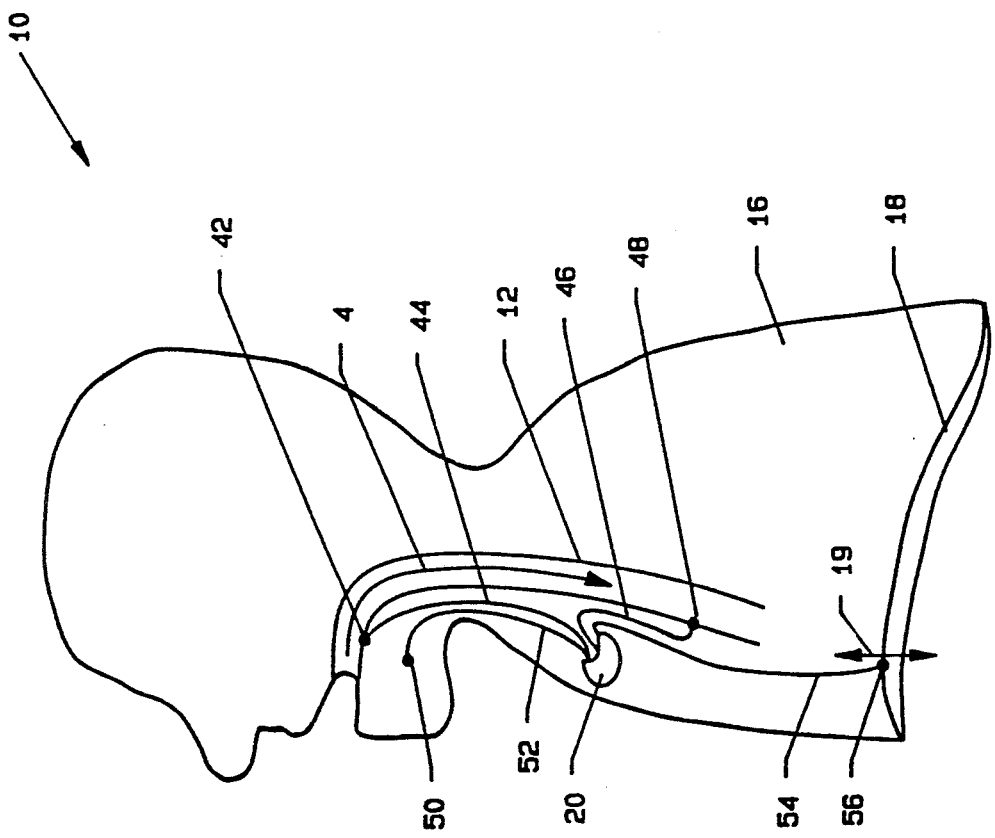
FIG. 4 is a schematic diagram of the respiratory system of a patient having a stimulation system according to the present invention.

FIG. 4 is a schematic diagram of patient 10 showing implantation of an electrical stimulation system for the treatment of both central and obstructive sleep apnea. Implantable pulse generator 20 is placed subcutaneously at a convenient position. Diaphragm 18 is electrically stimulated via electrode 56 coupled to lead 54.

Patency of upper airway 12 is monitored by pressure sensor 42 and pressure sensor 48 coupled to implantable pulse generator 20 via cables 44 and 46, respectively. Stimulation of the musculature of upper airway 12 is accomplished via lead 52 coupled to electrode 50. All other referenced elements are as previously described.

Figure 5:
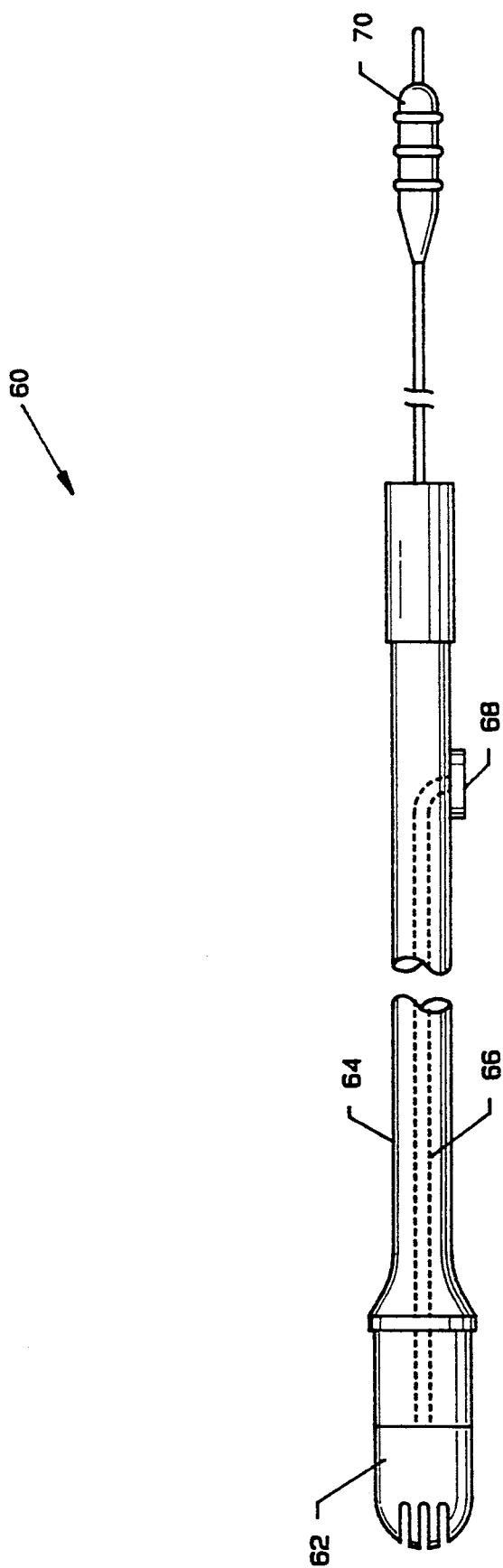
FIG. 5 is a plan view of a pressure transducer used to sense apnea events.

FIG. 5 is a plan view of a chronically implantable pressure transducer 60 similar to that implanted as pressure sensors 42 and 48 (see also FIG. 4). Distal end 62 of chronically implantable pressure transducer 60 contains a semiconductor sensing element properly packaged for chronic implantation. Lead body 64 optionally contains pressure reference lumen 66, which is coupled to pressure vent 68. Electrical connector 70 couples to implantable pulse generator 20. For additional construction details, the reader may consult U.S. Pat. No. 4,407,296 issued to Anderson incorporated herein by reference.

Figure 6:
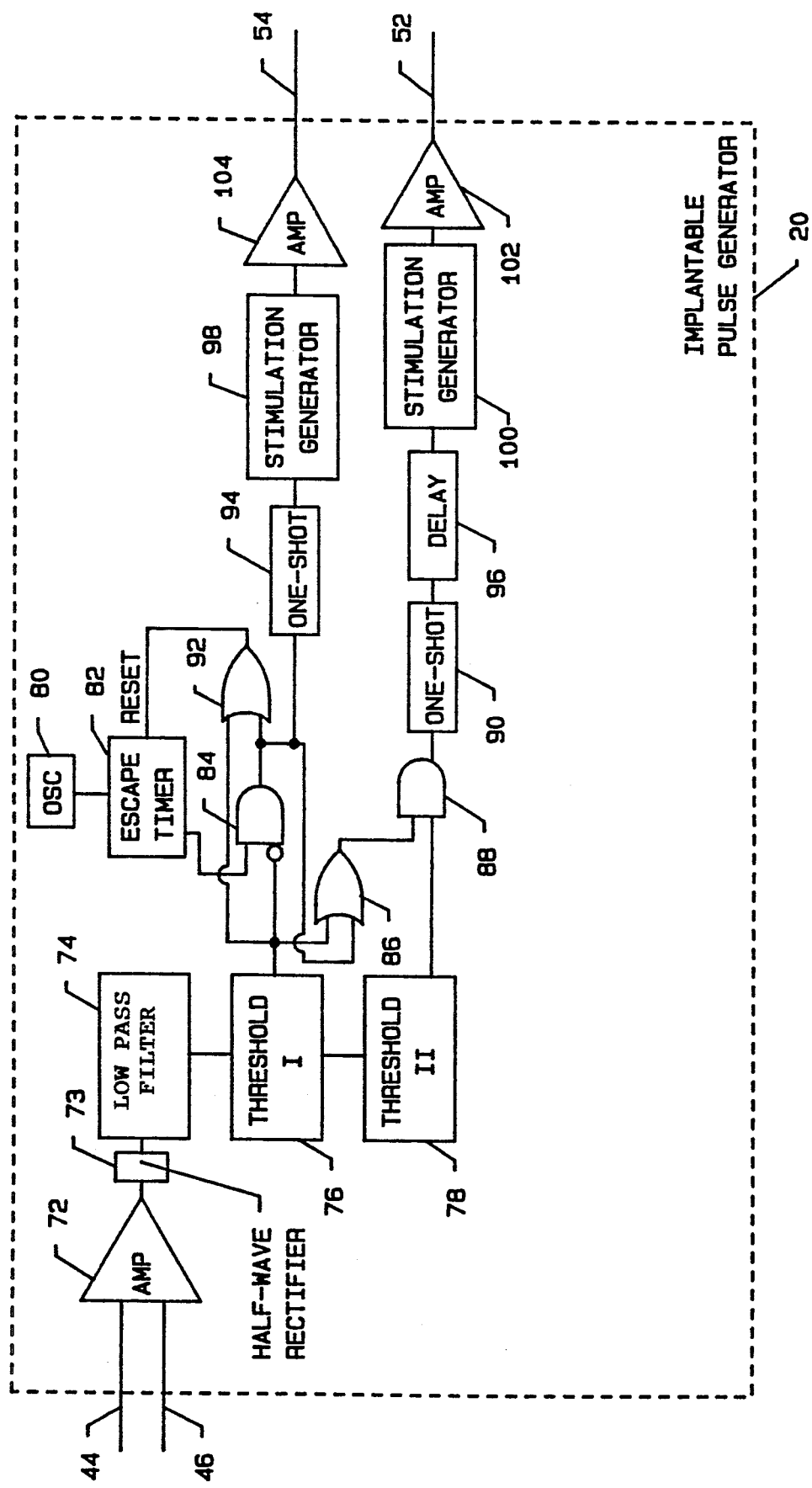
FIG. 6 is a block diagram of an implantable pulse generator.

FIG. 6 is a block diagram of implantable pulse generator 20 employing the present invention. The pressure measurements of upper airway 12 from pressure sensors 42 and 48 (see also FIG. 4) are provided by cables 44 and 46, respectively, to differential amplifier 72. The output of differential amplifier 72, which is more positive than negative, is rectified by half-wave rectifier 73 to eliminate the negative-going portion of the signal. This ensures that the resulting signal reflects pressure measurements of only the inspiratory portion of the respiration cycle.

The inspiration pressure signal is integrated by low pass filter 74 over a period which is less than the normal respiration cycle. Integration or filtering in this manner eliminates high frequency pressure spikes.

Circuit 76 monitors the inspiration signal in relationship to a first and lower threshold I. This first threshold is sufficient to determine only whether or not inspiration is in progress. The point is to make a determination of it and when inspiration begins. Circuit 76 provides a high binary output during inspiration, and a low binary output at all other times.

The output of circuit 76 is supplied to "or" gate 92 to provide a reset signal to escape timer 82 whenever inspiration begins. Escape timer 82 uses the output of oscillator 80 to determine the interval during which inspiration is anticipated. Should escape timer 82 finish counting the interval before "or" gate 92 provides a reset, the output of escape timer 82 provides a signal to "and" gate 84. If threshold I has not been reached at that time, "and" gate 84 provides an output to one-shot 94 for the generation of electrical stimulation of diaphragm 18 (see also FIG. 4).

The duration of electrical stimulation of diaphragm 18 is controlled by the output of one-shot 94. The electrical stimulation pulse train is generated by stimulation generator 98. The generated pulse train is amplified by output amplifier 104 and supplied to electrode 56 via lead 54 (see also FIG. 4).

The outputs of circuit 76 and "and" gate 84 are supplied to "or" gate 86. Thus "or" gate 86 provides an output whenever naturally initiated inspiration is sensed by circuit 76 or electrically stimulated by the output of "and" gate 84. This output is provided to "and" gate 88.

Circuit 78 monitors the inspiration signal and compares it to a higher threshold II. This threshold is set to distinguish between the normal increase in pressure of upper airway 12 associated with inspiration and the abnormal increase in pressure of upper airway 12 associated with obstructive sleep apnea. Such an abnormal pressure measurement causes circuit 78 to provide a binary high to "and" gate 88, which is "anded" with the inspiration signal from "or" gate 86. The output of "and" gate 88 is provided to one-shot 90 which provides a timed output to delay 96. Proper timing of the electrical stimulation of upper airway 12 is ensured by the output of delay 96. The pulse train is generated by stimulation generator 100 and amplified by output amplifier 102. The stimulation pulse train is supplied to electrode 50 via lead 52 (see also FIG. 4).

Figure 7:
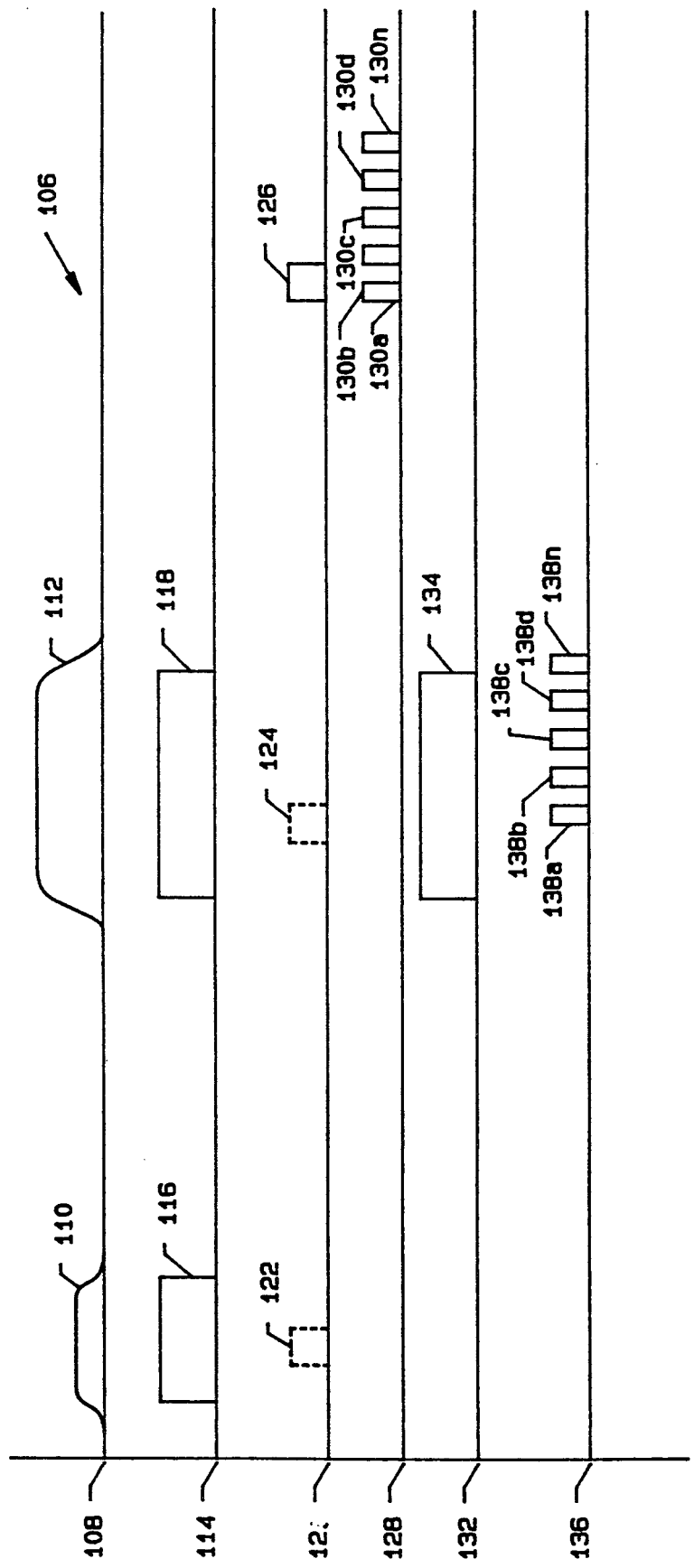
FIG. 7 is a graphical representation of the key signals of the implantable pulse generator.

FIG. 7 is a graphical representation of various key signals within implantable pulse generator 20. Curve 108 is the half-wave rectified output of low pass filter 74 (see also FIG. 6). Pulse 110 represents the pressure measurement for normal inspiration. Pulse 112 represents the pressure measurement for inspiration during an obstructive event during sleep. The absence of a pulse at time 106 represents a central sleep apnea event.

Curve 114 represents the output of circuit 76. Pulses 116 and 118 indicate detection of naturally occurring inspiration. No such detection is made at time 106. Curve 121 shows the output of escape timer 82. Pulses 122, 124, and 126 indicate the times before which inspiration should have occurred or a central sleep apnea event is assumed. Therefore, time 106 is assumed to be a central sleep apnea event.

The output of output amplifier 104 is represented by curve 128. An electrical stimulation pulse train consisting of pulses 130a–130n is generated beginning at time 106 in response to the assumption that a central sleep apnea event has occurred.

The output of circuit 78 is represented by curve 132. Because pulse 112 is in excess of threshold II (see also FIG. 6), pulse 134 is provided. Curve 136 represents the output of output amplifier 102. It consists of a stimulation pulse train of pulses 138a–138n generated in response to pulse 134.

Figure 8:
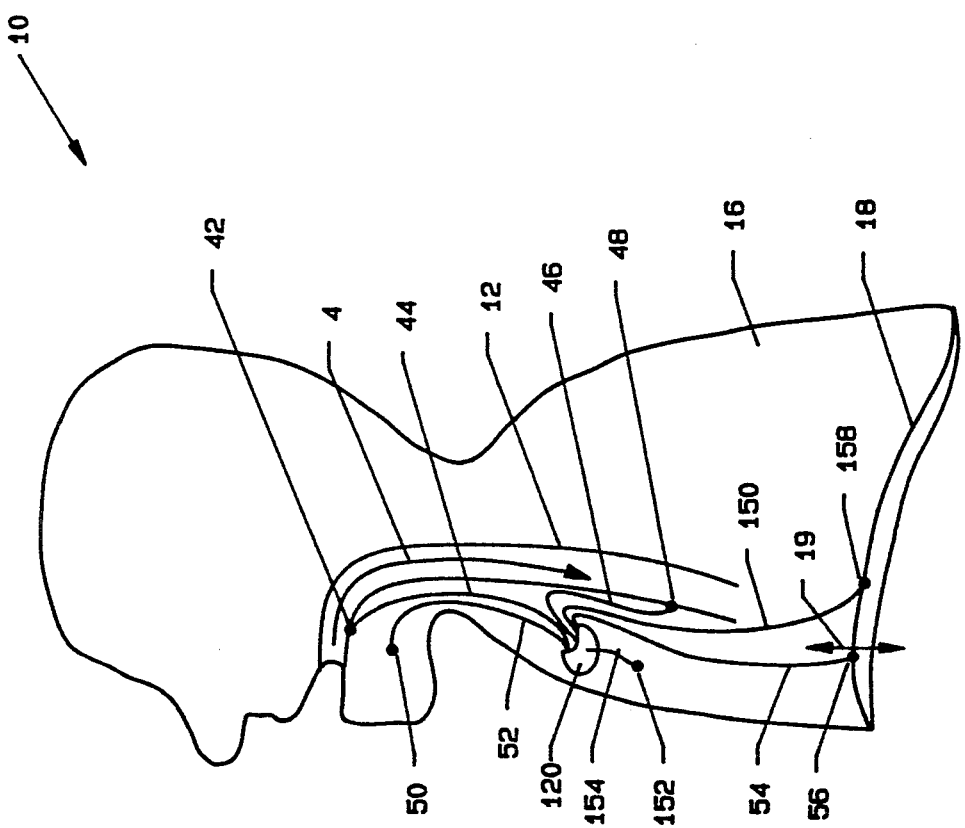
FIG. 8 is a schematic diagram of a stimulation system employing multiple sensors.

FIG. 8 is a schematic diagram of patient 10 having implanted a multiple sensor stimulation system. Sensor 158 is a standard neurological sensor coupled to the phrenic nerve. It transfers an electrical indication of neurological inspiratory drive to implantable pulse generator 120 via lead 150.

Sensor 152 is implanted within the cardiovascular system (e.g. right ventricle) of patient 10. It is coupled to implantable pulse generator 120 via lead 15 and is used to measure decreases in oxygen level of the blood which are indicative of an apnea event. Such measurements may be made on either the arterial or venous side of the cardiovascular system. Use of the arterial side is somewhat more difficult to access because of the pressure, but will ordinarily provide the more pronounced signal. The venous side yields a signal which tends to be integrated by the cardiovascular system to compensate for differences in oxygen content over a given normal respiratory cycle.

All remaining referenced elements are as previously discussed.

Figure 9:
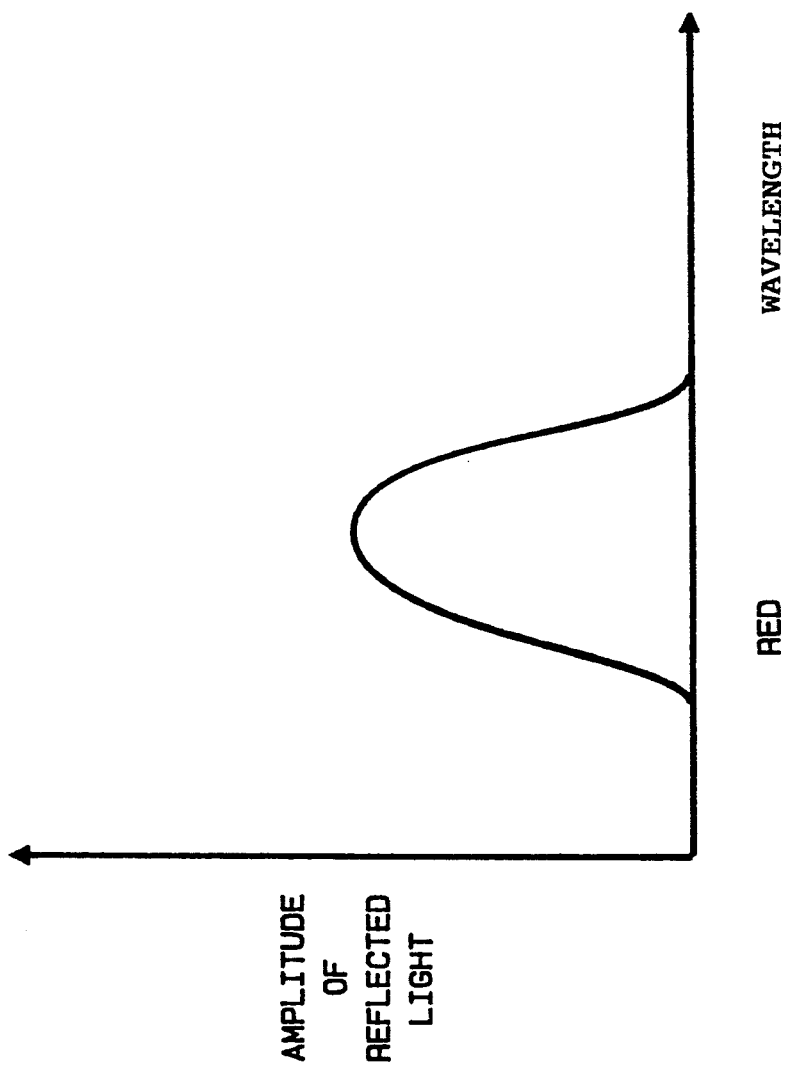
FIG. 9 is a graphical representation of the output of an oxygen sensor with normally oxygenated blood.

FIG. 9 is a graphical representation of the amplitude of reflected light within the blood of patient 10 wherein normal respiration is present. The reflected response is centered about the red wavelengths.

Figure 10:
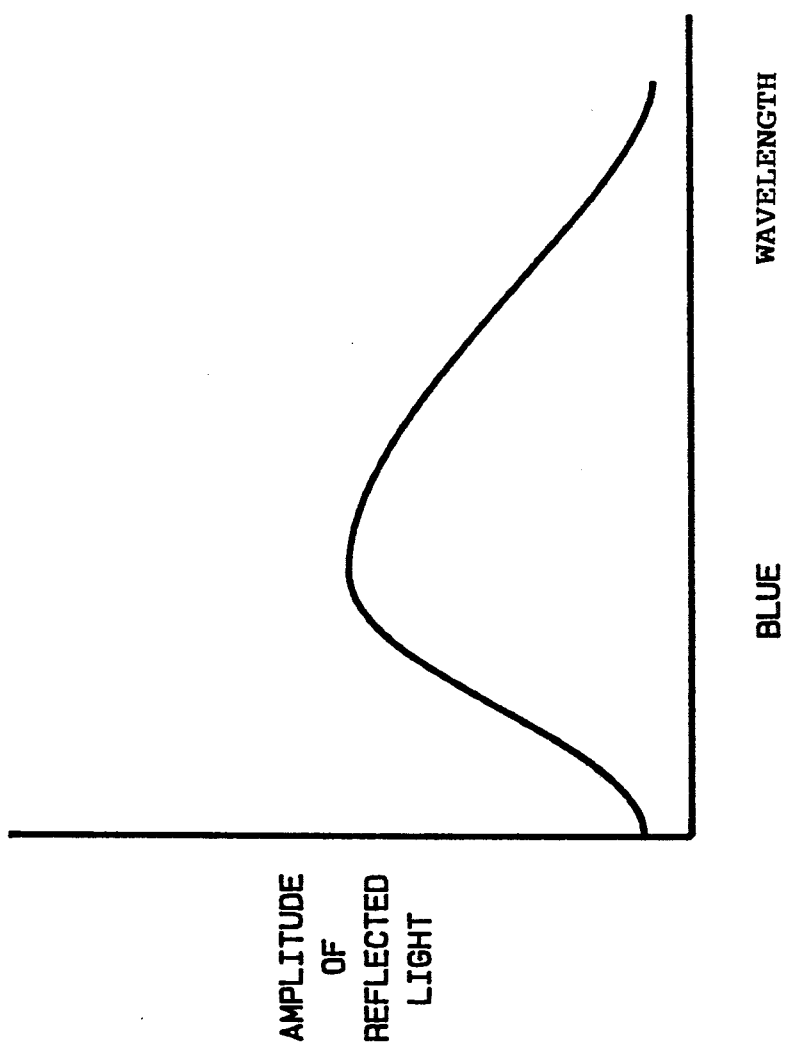
FIG. 10 is a graphical representation of the output of the oxygen sensor during an apnea event.

FIG. 10 is a graphical representation of the response of a reflectance oximeter within the blood of patient 10 during an apnea event. Note that the response is skewed toward the blue wavelengths.

Figure 11:
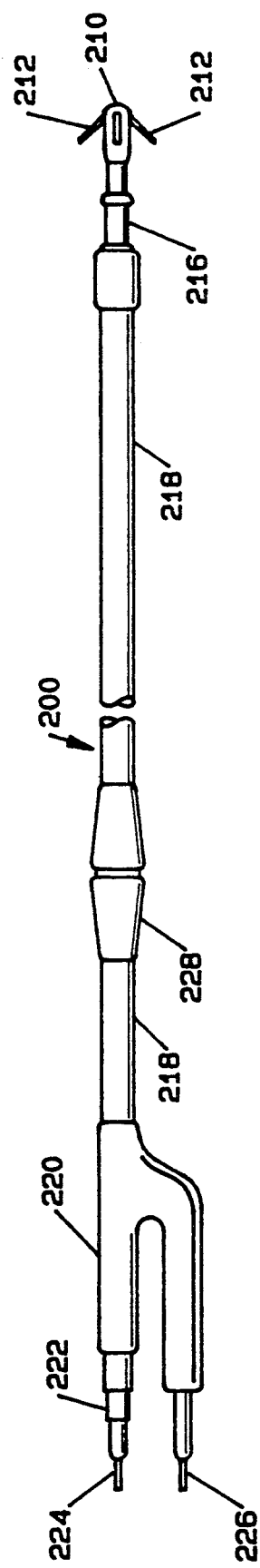
FIG. 11 is a plan view of an oxygen sensor.

FIG. 11 is a plan view of an oxygen sensor 200 implantable within the cardiovascular system of patient 10. Oxygen sensor 200 operates on the principle of reflectance oximetry as discussed in more detail below. Distal tip 210 is implanted transvenously into the right ventricle using standard techniques. It is held in place by tines 212.

Oximeter 216 emits light and measures the reflected response via an artificial sapphire window. Lead body 218 extends to connector 220 having terminal pin connectors 222, 224 and 226. Anchoring sleeve 228 provides for suturing of the proximal end without damage to the insulating sheath of lead body 218. Additional detail with regard to oxygen sensor 200 may be obtained from U.S. Pat. No. 4,813,421 issued to Baudino et al, incorporated herein by reference.

Figure 12:
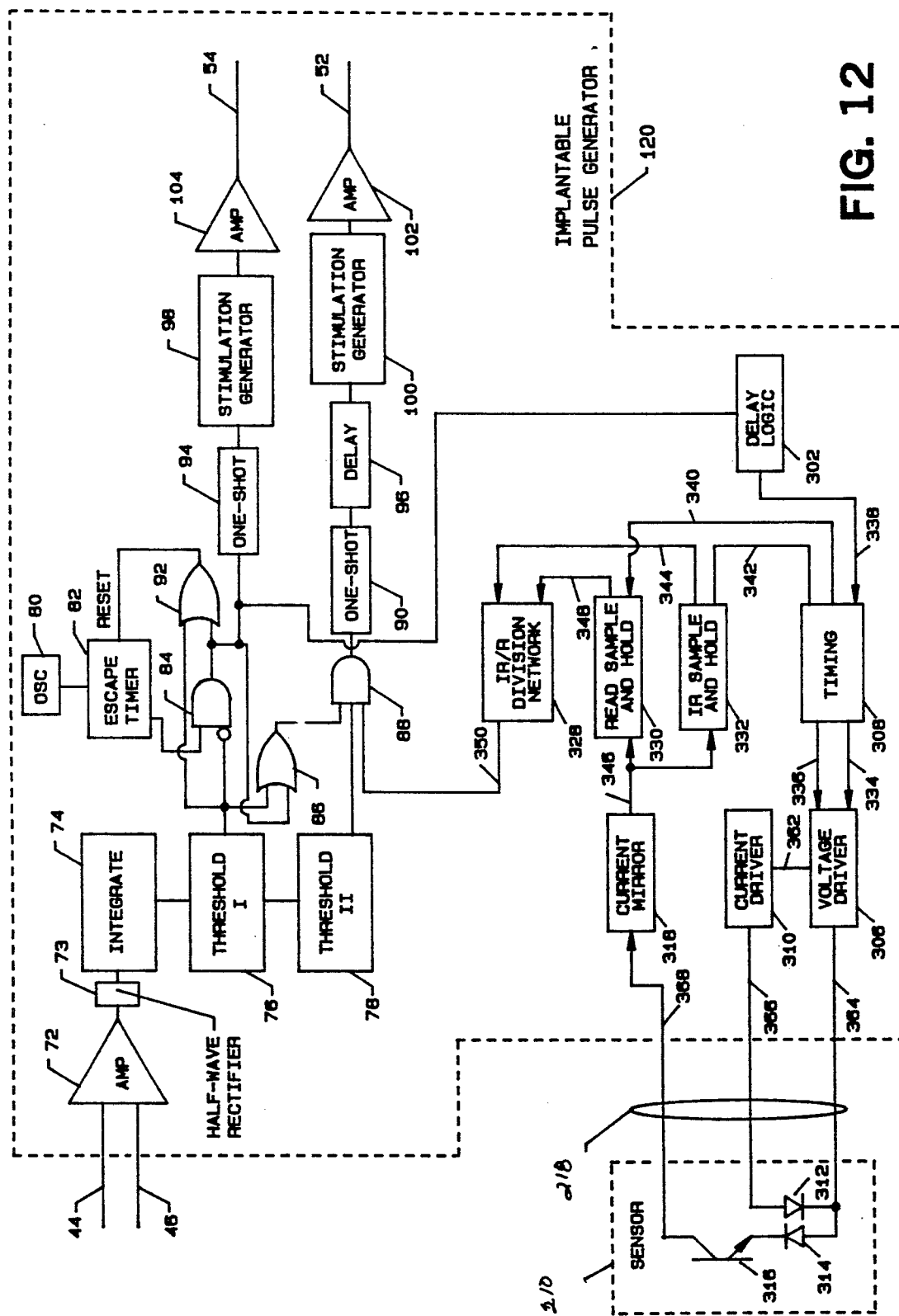
FIG. 12 is a block diagram of an implantable pulse generator in a multiple sensor system.

FIG. 12 is a block diagram of implantable pulse generator 120 as used in a multiple sensor stimulation system. In this particular example, and not to be deemed limiting of the present invention, two sensors (i.e. pressure and blood oxygen) are used. Distal tip 210 of oxygen sensor 200 contains the sensing element as explained above. This sensing element functions as a reflectance oximeter which emits light from light emitting diode 312 into the blood and senses the reflected response by photo sensitive element 316. Diode 314 permits oxygen sensor 200 to function with only the three conductors 364, 366, and 368.

Power to light emitting diode 312 is supplied from current driver 310 and voltage driver 306, as coupled by line 362. Timing of this drive is provided by timing circuit 308 via lines 334 and 336. These timing signals are synchronized to the pressure sensing circuitry by delay logic 302 coupled to timing circuit 308 by line 338.

Current mirror 318 receives the return signal via conductor 368. The infrared signal is channeled to sample and hold circuit 332 by line 346. The control signal is similarly transferred to sample and hold circuit 330 by line 346. The output of each is gated in turn to division network 328 via lines 344 and 348 under control of timing signals received via lines 340 and 342.

Division network 328 compares the two signals to look for the color shift from red to blue (see also FIGS. 9 and 10) which signals an apnea event. The output is coupled via line 350 to "and" gate 88. In this manner, stimulation generator 100 is not triggered unless both oxygen and pressure sensors detect a probable apnea event. All other referenced elements are as previously described.

Having thus described the preferred embodiments of the present invention, those of skill in the art will be readily able to apply the teachings found herein to yet other embodiments within the scope of the claims hereto attached.

We claim:
1. An apparatus comprising:
    a. first means for sensing a central apnea event;
    b. first means responsibly coupled to said first sensing means for providing stimulation to a diaphragm of a patient in response to sensing of said central apnea event;
    c. second means coupled to said first sensing means for sensing an obstructive apnea event; and,
    d. second means coupled to said second sensing means for generating electrical stimulation of muscles of said patient in response to sensing by said second sensing means of said obstructive apnea event.

2. An apparatus according to claim 1 wherein said first sensing means further comprises a pressure sensor.

3. An apparatus according to claim 2 wherein said second sensing means comprises a pressure sensor.

4. An apparatus according to claim 3 wherein said first sensing means further comprises a first threshold circuit.

5. An apparatus according to claim 4 wherein said second sensing means further comprises a second threshold circuit.

6. An apparatus according to claim 1 wherein said first sensing means comprises a means for measuring blood oxygen.

7. An apparatus according to claim 6 wherein said measuring means comprises a reflectance oximeter.

8. An apparatus according to claim 1 wherein said first sensing means comprises means for determining a plurality of conditions related to apnea.

9. An apparatus according to claim 8 wherein said determining means comprises an oximeter.

10. An apparatus according to claim 8 wherein said determining means comprises a pressure sensor.

11. An apparatus according to claim 8 wherein said determining means comprises a nerve electrode.

12. A method of treating a patient comprising:
   a. sensing pressure within an upper airway of said patient;
   b. assuming a central apnea event if said pressure does not reach a first threshold within a predetermined period of time;
   c. electrically stimulating a diaphragm of said patient in response to said central apnea event assumption;
   d. assuming an obstructive apnea event if said pressure reaches a second threshold; and,
   e. electrically stimulating muscles of said patient in response to said assuming said obstructive apnea event.

* * * * *